United States Patent
Hahn et al.

(10) Patent No.: US 6,843,240 B1
(45) Date of Patent: Jan. 18, 2005

(54) METHOD FOR MONITORING THE FUNCTIONING OF A NOX SENSOR ARRANGED IN AN EXHAUST GAS CHANNEL OF AN INTERNAL COMBUSTION ENGINE

(75) Inventors: Hermann Hahn, Lehre (DE); Axel Lang, Wolfenbuttel (DE)

(73) Assignee: Volkswagen AG, Wolfsburg (DE)

( * ) Notice: Subject to any disclaimer, the term of this patent is extended or adjusted under 35 U.S.C. 154(b) by 0 days.

(21) Appl. No.: 10/088,466

(22) PCT Filed: Sep. 15, 2000

(86) PCT No.: PCT/EP00/09071

§ 371 (c)(1),
(2), (4) Date: Jul. 10, 2003

(87) PCT Pub. No.: WO01/21951

PCT Pub. Date: Mar. 29, 2001

(30) Foreign Application Priority Data

Sep. 22, 1999 (DE) .......................................... 199 45 374

(51) Int. Cl.[7] .............................................. F02D 41/00
(52) U.S. Cl. ........................... 123/688; 60/277; 60/281; 60/295; 60/301
(58) Field of Search ................................. 123/295, 443, 123/672, 688; 60/277, 281, 295, 299, 301

(56) References Cited

U.S. PATENT DOCUMENTS

| | | | | |
|---|---|---|---|---|
| 5,341,642 A | * | 8/1994 | Kurihara et al. ............... | 60/277 |
| 5,426,934 A | | 6/1995 | Hunt et al. .................... | 60/276 |
| 5,558,752 A | * | 9/1996 | Wang et al. ................. | 123/672 |
| 5,568,725 A | * | 10/1996 | Uchikawa ..................... | 60/277 |
| 5,797,384 A | | 8/1998 | Kitagawa et al. ........... | 123/674 |
| 6,539,705 B2 | * | 4/2003 | Beer et al. .................... | 60/277 |
| 6,772,585 B2 | * | 8/2004 | Iihoshi et al. ................. | 60/277 |
| 2001/0032456 A1 | * | 10/2001 | Yonekura et al. ............. | 60/277 |
| 2002/0038544 A1 | * | 4/2002 | Ikemoto et al. ............... | 60/285 |
| 2003/0010016 A1 | * | 1/2003 | Beer et al. .................... | 60/277 |
| 2003/0061803 A1 | * | 4/2003 | Iihoshi et al. ................. | 60/285 |
| 2003/0221667 A1 | * | 12/2003 | Surnilla ...................... | 123/672 |
| 2004/0040289 A1 | * | 3/2004 | Mazur et al. ................. | 60/295 |

FOREIGN PATENT DOCUMENTS

| | | |
|---|---|---|
| DE | 19539024 | 4/1996 |
| DE | 19651559 | 6/1997 |
| DE | 19752271 | 6/1998 |
| DE | 19830829 | 4/1999 |
| DE | 19808382 | 9/1999 |
| DE | 19823921 | 12/1999 |
| EP | 0916941 | 5/1999 |

* cited by examiner

Primary Examiner—Erick Solis
(74) Attorney, Agent, or Firm—Baker Botts L.L.P.

(57) ABSTRACT

The invention relates to a method for monitoring the functioning of an NOx sensor, which is arranged in an exhaust gas channel of an internal combustion engine and is located downstream from an NOx storage catalytic converter. The aim of the invention is to detect the faulty functioning of the NOx sensor in a simple manner in order to be able to take appropriate measures if necessary. To this end, the mass of NOx absorbed by the NOx storage catalytic converter is determined within a diagnostic period using a measurement signal of the NOx sensor. At the same time, an absorbed NOx target mass is calculated using a model for the NOx storage catalytic converter. A ratio of the NOx mass to the NOx target mass is then compared to predetermined limit values to determine the functioning of the NOx sensor. The aim of the invention is alternatively accomplished by measuring a duration time for a complete NOx regeneration of the NOx storage catalytic converter. A specified duration time is also calculated for the NOx regeneration using a model for the NOx storage catalytic converter and using a measured or calculated NOx load state. A ratio of the measured duration time to the specified duration time is then compared to predetermined limit values to determine the functioning of the NOx sensor.

7 Claims, 2 Drawing Sheets

METHOD FOR MONITORING THE FUNCTIONING OF A NOX SENSOR ARRANGED IN AN EXHAUST GAS CHANNEL OF AN INTERNAL COMBUSTION ENGINE

BACKGROUND OF THE INVENTION

The invention relates to a process for monitoring the function of an NOx sensor arranged in an exhaust duct of an internal combustion engine. To reduce the emission of pollutants from an internal combustion engine, a known practice is to arrange suitable catalysts in the exhaust gas duct of the engine. The catalyst collects pollutants, such as CO, HC or $H_2$ that can act as reducing agents and be oxidized by atmospheric oxygen. These reducing agents may also react with the NOx, produced during the combustion process in the engine, to form nitrogen.

If the engine is operating in a lean mode the proportion of oxygen in the air-fuel mixture is increased, which is more favorable to combustion, and as a consequence the proportion of the reducing agents in the exhaust will decrease. In this case, an adequate reaction of NOx on the catalyst will no longer be ensured. As a remedy, an NOx reservoir may be arranged in the exhaust duct and combined with the catalysts to make an NOx storage catalyst. The NOx storage catalyst will absorb NOx if the NOx desorption temperature is not exceeded or until the NOx storage capacity is reached. Prior to reaching it's storage capacity, the system will have to change to a regeneration mode to regenerate the NOx storage catalyst by a period of rich operation, and prevent NOx emission.

To determine whether regeneration is necessary the NOx concentration downstream from the NOx storage catalyst may be detected with an NOx sensor. A disadvantage of this, however, is that if the NOx sensor misfunctions, high NOx emissions may occur, or NOx may be unnecessarily consumed during a premature regeneration. The object of the present invention is to detect misfunctions of the NOx sensor in a simple manner so appropriate countermeasures may be adopted if necessary.

SUMMARY OF THE INVENTION

The object of the invention is accomplished by a method of monitoring the functioning of an NOx sensor. During a diagnostic period the levels of NOx not absorbed by the NOx storage catalyst are detected by the sensor and accumulated. From the levels detected by the sensor the mass of NOx absorbed by the storage catalyst during this diagnostic period may be determined. At the same time, a target mass of NOx absorbed may be calculated using a model of the NOx storage catalyst. The ratio of the detected NOx mass absorbed, to the NOx target mass calculated is then determined and compared to a lower bound and an upper bound. If the mass ratio falls below the lower bound or above the upper bound a maintenance signal may then be generated.

In a second embodiment, the function of an NOx sensor is monitored by determining a duration time for a complete NOx regeneration of the NOx storage catalyst. A target duration time for a complete NOx regeneration may then be determined from a model of the NOx storage catalyst and a measured or calculated NOx loading condition. The ratio of the duration time determined for a complete NOx regeneration, to the measured or calculated target duration time is then calculated and compared to a lower bound and an upper bound. If the time ratio falls below the lower bound or above the upper bound a maintenance signal may then be generated.

After the occurrence of a maintenance signal, in either situation, the error can be corrected by suitable measures, or the NOx sensor can be replaced if necessary. Further, it is advantageous to set the period of diagnosis to begin immediately after a complete NOx regeneration of the NOx storage catalyst and a change to a lean mode of the engine. Preferably, the period of diagnosis will end after identification of a need to regenerate the NOx storage catalyst or upon a change in regeneration mode. Monitoring the function of the NOx sensor should preferably take place only when a selected period of constant lean mode of operation of the engine has been detected. In this way, the influences from the dynamic operation of the engine on the model of the storage catalyst, that are difficult to allow for, can be avoided.

For a better understanding of the present invention, together with other and further objects thereof, reference is made to the following description, taken in conjunction with the accompanying drawings, and its scope will be pointed out in the appended claims.

DESCRIPTION OF THE INVENTION

Figure 1:
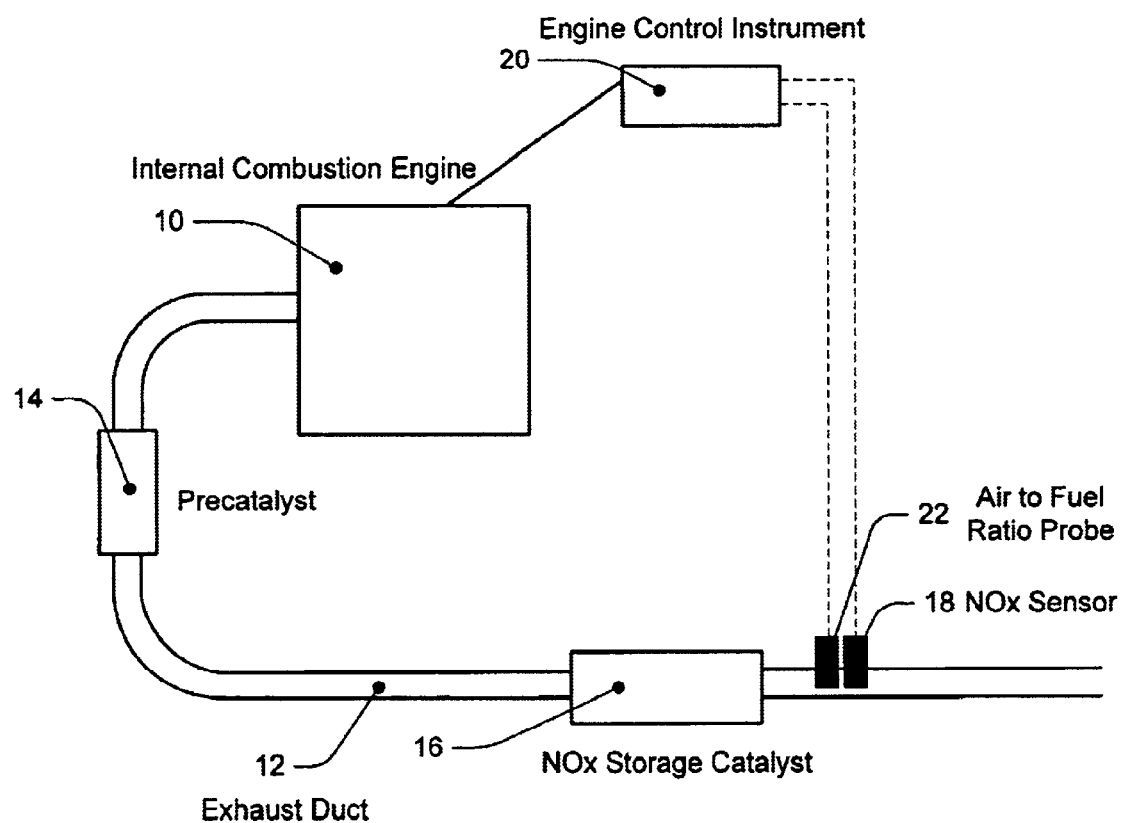
FIG. 1 is a schematic diagram depicting the arrangement of an internal combustion engine having an exhaust duct, a precatalyst, a NOx storage catalyst and an NOx sensor.
Figure 2:
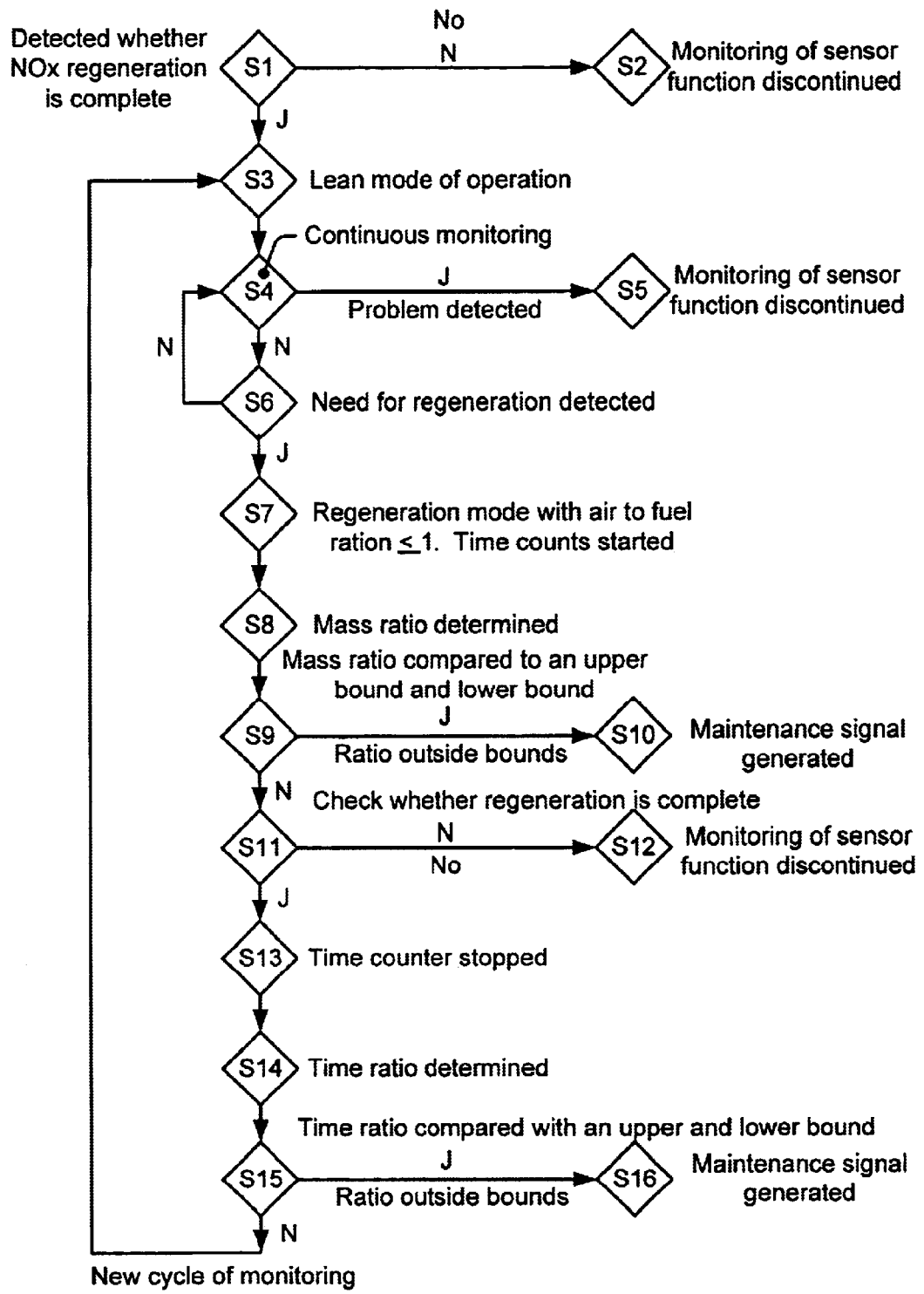
FIG. 2 is a flow diagram of a method for monitoring the function of the NOx sensor according to an embodiment of the invention.

FIGS. 1 and 2 are drawings showing embodiments of the invention. FIG. 1 shows an arrangement of an internal combustion engine 10, including an exhaust duct 12, a precatalyst 14, and a NOx storage catalyst 16. The precatalyst 14, and the NOx storage catalyst 16, serve to diminish pollutant emission of the engine 10. Ordinarily, the catalysts 14 and 16 include components that make possible the oxidation of reducing agents formed during combustion, such as CO, HC or $H_2$, by atmospheric oxygen. At least the NOx storage catalyst 16, comprises a catalyst component that makes possible the reduction of NOx, formed during the process of combustion of an air-fuel mixture, by means of the reducing agents. If the engine 10, is in a lean mode of operation, as a rule, the proportion of reducing agents in the exhaust will not be sufficient to ensure a high conversion of NOx. In lean mode, therefore, the NOx will be absorbed as nitrate by the storage component of the NOx storage catalyst 16.

The absorption of the NOx can take place only until either an NOx desorption temperature is exceeded or the NOx storage capacity is exhausted. Before this point, therefore, the system must change into a regeneration mode, with an air to fuel ratio $\leq 1$, to cause NOx regeneration. Whether there is a need for regeneration will be determined by the NOx concentration or emission detected by the NOx sensor 18. A test signal will be passed on to an engine control instrument 20, evaluated, and used to control the operating mode of the engine 10.

FIG. 2 shows a block diagram which depicts a monitoring of the function of the NOx sensor 18, during dynamic operation of the engine 10. For example, In step S1, it is first detected whether a complete NOx regeneration of the NOx storage catalyst 16, has been carried out. If this is not the case, then the monitoring of the function of the sensor 18, is discontinued (step S2). If complete regeneration of the NOx storage catalyst has been carried out a lean mode will begin step S3.

At the beginning of the lean mode (step S3), a determination of an NOx mass absorbed in the NOx storage catalyst 16, is started. During a preassigned period of diagnosis, the NOx concentration downstream from the NOx storage catalyst 16, is detected by the NOx sensor 18. This detected concentration is accumulated, and then deducted from a measured or calculated crude NOx emission of the engine 10. Second, with the aid of known models of the NOx storage catalyst 16, and from the crude NOx emission, a target mass of absorbed NOx is calculated. The target NOx mass corresponds to a maximum NOx mass that can be absorbed by a fresh NOx storage catalyst 16.

In step S4, the engine 10, is checked continuously to determine whether it is in constant lean operation during the period of diagnosis. In the case of disturbances due to dynamic processes, for example a change in a homogeneous mode or an abrupt shutdown, the target NOx mass calculated for the period of diagnosis is especially prone to error, and therefore the monitoring of function is broken off (step S5). Preferably, the period of diagnosis is determined so that it begins with the change in the lean mode (step S3) and continues until a need for regeneration is detected (step S6).

Such a need for regeneration may for example be detected by way of the NOx sensor 18, in the form of a threshold emission for NOx. Once the need for regeneration is present, a change into the regeneration mode with an air to fuel ratio $\leq 1$ is initiated (step S7). Simultaneously, a time counter is started, to determine a duration time for a complete NOx regeneration.

From the absorbed NOx mass found by way of the NOx sensor 18, for the NOx storage catalyst 16, and the target NOx mass, a mass ratio is determined in a step S8. In step S9, if the mass ratio is above an upper bound or below a lower bound, then there is a defect in the NOx sensor 18, and a maintenance signal is generated (step S10). The upper mass ratio bound usually reflects a ratio of the NOx mass found by way of the NOx sensor 18, to the target NOx mass in a fresh NOx storage catalyst 16.

If the mass ratio lies between the two bounds, then in a step S11 it can be checked whether the NOx regeneration has been carried out completely. For this purpose, for example, a probe 22, that measures the air to fuel ratio, arranged downstream from the NOx storage catalyst 16, is suitable. Towards the end of the NOx regeneration, the value of the air to fuel ratio declines distinctly, and for example by preassignment of a suitable threshold value, a stop signal can be set for the time counter (step S13). If the NOx regeneration is discontinued prematurely, the functional monitoring of the NOx sensor 18, will be broken off in step S12.

With the aid of the model of the storage catalyst, a target duration time for the NOx regeneration is calculated from a measured or calculated state of NOx loading. In step S14 a time ratio will be determined by taking the ratio of the duration time, determined in step S7, to the target duration time. In step S15 the time ratio is compared with an upper bound or a lower bound. If the time ratio is above the upper bound or below the lower bound, there is a sensor defect, and a maintenance signal is generated (step S16). If this is not the case, then a new cycle of functional monitoring, beginning with step S3, may be initiated. The upper bound is again so chosen that it reflects a ratio of the duration time to the target duration time in a fresh NOx storage catalyst 16.

Sensor plausibility is also checked to determine whether a lesser measure of storage fill is yielded, for example, as may occur with poorer storage behavior of the catalyst or when the measured regeneration time required is reduced to a corresponding extent.

While there have been described what are believed to be the preferred embodiments of the invention those skilled in the art will recognize that other changes and modifications may be made thereto without departing from the spirit of the invention, and it is intended to claim all such changes and modifications as fall within the true scope of the invention.

What is claimed is:

1. A process for monitoring the function of a NOx sensor arranged in an exhaust duct of an internal combustion engine downstream from a NOx storage catalyst, comprising:
    (a) monitoring and accumulating NOx levels detected by said sensor during a diagnostic period;
    (b) determining a mass of absorbed NOx by said NOx storage catalyst as a difference between engine NOx emissions and said accumulated NOx levels detected by said sensor;
    (c) calculating a target mass of absorbed NOx from a model of said NOx storage catalyst; and
    (d) determining a mass ratio of said absorbed NOx mass to said target NOx mass and comparing said mass ratio with at least one of a lower bound and an upper bound.

2. A process according to claim 1, further comprising comparing said mass ratio to both said lower bound and said upper bound and generating a maintenance signal when said mass ratio is below said lower bound and generating a maintenance signal when said mass ratio is above said upper bound.

3. A process according to claim 1, wherein said diagnostic period begins immediately after a complete NOx regeneration of said NOx storage catalyst and a return to a lean mode of operation of said internal combustion engine.

4. A process according to claim 3, wherein said diagnostic period ends after identification of a need for regeneration of said NOx storage catalyst.

5. A process for monitoring the function of a NOx sensor arranged in an exhaust duct of an internal combustion engine downstream from a NOx storage catalyst which comprises:
    (a) determining a duration time for a NOx regeneration of said NOx storage catalyst;
    (b) calculating a target duration time for said NOx regeneration using a model of said NOx storage catalyst and NOx loading; and
    (c) determining a time ratio of said duration time to said target duration time and comparing said time ratio with one of a lower bound and an upper bound.

6. A process according to claim 5, further comprising comparing said time ratio to both said lower bound and said upper bound and generating a maintenance signal when said time ratio is below said lower bound and generating a maintenance signal when said time ratio is above said upper bound.

7. A process according to any of the preceding claims, wherein said monitoring the function of said NOx sensor takes place only during a selected period of lean operation of said internal combustion engine.

* * * * *